US00PP37504P2

(12) United States Plant Patent
Hansen

(10) Patent No.: US PP37,504 P2
(45) Date of Patent: Jun. 30, 2026

(54) ***EPIMEDIUM* PLANT NAMED 'Carnival Clown'**

(50) Latin Name: ***Epimedium* hybrid**
Varietal Denomination: Carnival Clown

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 33 days.

(21) Appl. No.: 18/831,926

(22) Filed: Nov. 13, 2025

(51) Int. Cl.
*A01H 6/00* (2018.01)
*A01H 5/02* (2018.01)

(52) U.S. Cl.
USPC ..... Plt./429

(58) Field of Classification Search
USPC ..... Plt./429
CPC ..... A01H 6/00; A01H 5/02
See application file for complete search history.

*Primary Examiner* — Keith O. Robinson

(57) ABSTRACT

A new cultivar of *Epimedium* plant named 'Carnival Clown' characterized by its medium-sized perennial habit and evergreen foliage with flowering in panicles beginning in the late spring that have spurs with yellowish tips and centers and bright orange in the middle. The sepals are vivid reddish-orange. The foliage has three lanceolate leaflets with small marginal teeth, with a light chartreuse with bronze coloring in cooler conditions and becoming deep green in summer.

1 Drawing Sheet

Botanical denomination: *Epimedium* hybrid.
Variety designation: 'Carnival Clown'.

STATEMENT REGARDING PRIOR DISCLOSURES UNDER 37 CFR 1.77(B)(6)

The Applicant asserts that no publications or advertisements relating to sales, offers for sale, or public distribution occurred more than one year prior to the effective filing date of this application. The first offer for sale was by Walters Gardens, Inc. on Nov. 13, 2024, to Garden State Growers. Walters Gardens, Inc. obtained the new plant and all information about the new plant directly from the inventor. Any information or disclosure about the claimed plant less than one year prior to the effective filing date of this application would have been obtained directly or indirectly from the Inventor and would be a 35 U.S.C. 102(b) exception.

BACKGROUND OF THE INVENTION

The present invention relates to a new and distinct Barrenwort plant from the genus *Epimedium* and given the cultivar name 'Carnival Clown'. The new plant was the result of a single seedling selection from a cross on Apr. 30, 2014, by the inventor between 'Amber Queen' U.S. Plant Pat. No. 17,197 as the female or seed parent and *Epimedium* x *omeiense* 'Rigoletto' (not patented) as the male or pollen parent. The seeds from the pollination were collected in May of 2014. The individual seedling was given the breeder code 14-3-21 and was first isolated from trials at a nursery in Zeeland, MI during April of 2016. It was selected for the final introduction in April of 2019 and later named 'Carnival Clown'.

*Epimedium* 'Carnival Clown' has been asexually propagated at the same nursery in Zeeland, MI by division of the rhizome in 2016 and found to reproduce plants that are identical and exhibit all the characteristics of the original plant in successive generations of asexual propagation.

*Epimedium* 'Carnival Clown' has not been observed under all possible environments. The phenotype may vary slightly with different environmental conditions, such as temperature, light, fertility, moisture and maturity levels, but without any change in the genotype.

In comparison to the new plant, the female parent has flowers with less reflexed and broader spurs of light yellow without any orangish coloration. The male parent has a smaller denser habit with deep reddish flower spurs, with fewer flowers per inflorescence, the inflorescence is more horizontal, and the foliage is less blushed with bronze.

The nearest comparison varieties known to the inventor are: 'Dream Catcher' U.S. Plant Pat. No. 36,549 and 'Jester's Hat' U.S. Plant Pat. No. 37,187.

'Dream Catcher' has larger inflorescences with more numerous smaller flowers with light yellow spur tips and reddish sepals. 'Jester's Hat' has a similar habit in both height and width but has flowers with deeper golden-yellow spurs with red sepals.

*Epimedium* 'Carnival Clown' is distinct from the parents and all other *Epimedium* known to the inventor in the following combined traits:

1. Medium-sized evergreen perennial;
2. Medium-sized flowers with spurs having yellowish tips and centers with the middle potion bright orangish, and sepals of vivid reddish orange on airy branched panicles beginning in late spring;
3. Tri-parted foliage has lanceolate leaflets with small marginal teeth, light chartreuse with bronze coloring in cooler conditions becoming medium green in the heat of summer.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, temperature, source, and direction may cause the appearance of minor variations in color.

DETAILED PLANT DESCRIPTION

Figure 1:
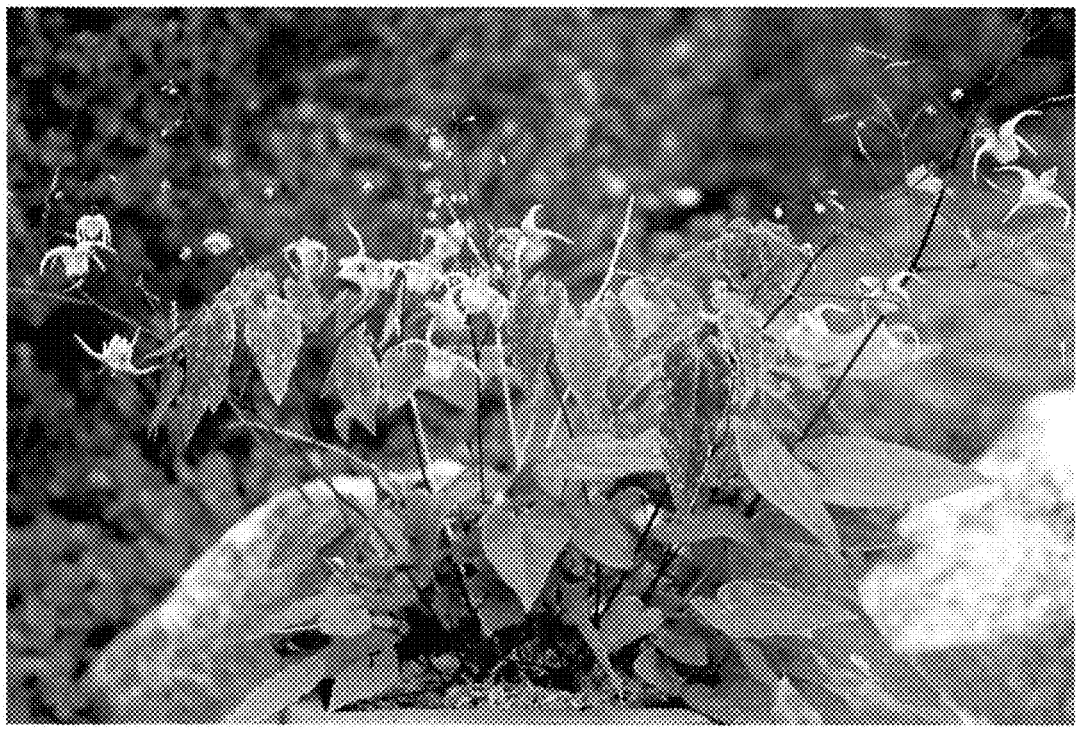
FIG. 1 shows a landscape view of a two-year-old plant in mid-season flower in an overwintered trial block at a nursery near Zeeland, Michigan.
Figure 2:
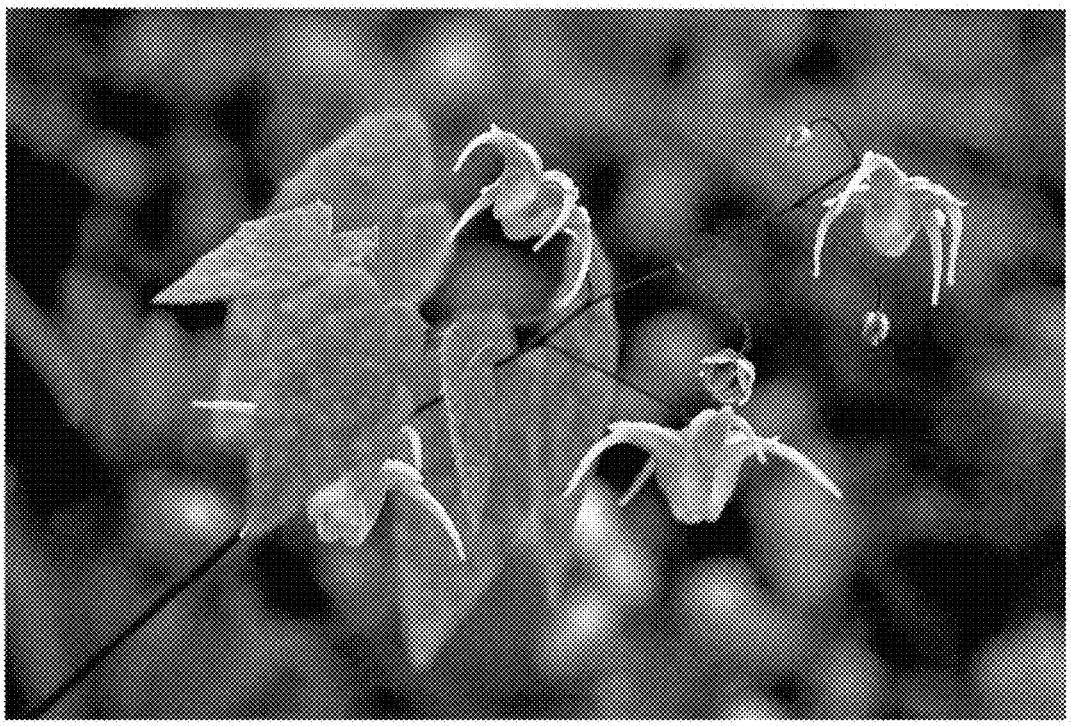
FIG. 2 shows a close-up of a scape with flowers and buds.

The following is a detailed description of the new *Epimedium* cultivar 'Carnival Clown' based on observations of a two-year-old specimen grown in a shaded greenhouse in Zeeland, Michigan with supplemental watering and fertilizer as needed. Color descriptions are from the 2015 edition of The Royal Horticultural Society Colour Chart except where common dictionary terms are used.

Parentage: The female parent is 'Amber Queen', the male parent is 'Rigoletto';

Propagation: Rhizome divisions;

Growth rate: Moderate;

Root development: Initiating in about 6 weeks;

Crop time: Finishing in a 3.8-liter pot from a 50 mm plug in 10 to 12 weeks;

Plant size: Soil level to top of foliar plane to about 44 cm tall and to about 90 cm wide, soil level to top of floral plane about 62 cm;

Root description: Dense, fibrous roots on rhizomes;

Rhizomes: Surface smooth, matte, glabrous; to about 12 mm in length and 5 mm in diameter; color nearest RHS 186D;

Branching habit: Branches arise from rhizome;

Stem: Cylindrical; moderately glossy; glabrate to sparsely puberulent; strong; stiff; about 30 cm in length and 2 mm in diameter at base;

Stem color: Variable; older stems between RHS 178A and RHS 177A; young stems between RHS 148B and RHS 178B;

Stem aspect: Initially upright and arching with maturity;

Internode length: 30 cm;

Leaf: Typically one or two tri-parted leaf per node; to 20 cm long and 19 cm wide;

Leaflets: Three; lanceolate; stiff; acute apex; cordate, rarely; slightly undulate; finely serrulate with stiff, sharply-pointed, small spines 1 mm to 1.5 mm long and to 1 mm in width; center leaflet to 13.5 cm long and 6.5 cm wide; side leaflets to 13 cm long and 6 cm wide; both lobes on center leaflets to 3 cm long and 2.5 cm wide; outer lobe on side leaflets to 4 cm long and 3 cm wide, inner lobe to 2.2 cm long and 2.8 wide;

Leaflet surface: Adaxial smooth; glabrous; highly lustrous; abaxial smooth, glabrous, matte;

Leaflet color: Young adaxial between RHS 144A and RHS 144B with irregular blotches of nearest RHS 176B, young abaxial nearest RHS 138B with irregular blotches of between RHS 187A and RHS 183B; mature adaxial between 137B and RHS 138A, mature abaxial between RHS 189A and RHS N138C;

Leaflet venation: Pinnate; glabrous adaxial and abaxial; adaxial lightly indented; abaxial slightly costate;

Leaflet venation color: Adaxial nearest RHS 138B, abaxial midrib between RHS 160C and RHS 161C, primary veins between RHS 146D and RHS 148D, secondary veins nearest RHS 137D;

Petioles: Arising from rhizome; cylindrical; glabrous to sparsely puberulent; slightly lustrous; stiff; to 30 cm long and 2.5 mm diameter;

Petiole color: Older petioles between RHS 178A and RHS 177A; young stems between RHS 148B and RHS 178B;

Petiolules: Cylindrical; smooth; slightly lustrous; stiff; to about 7 cm long and 1 mm diameter on center leaflets and to about 4 cm long and 0.7 mm diameter on side leaflets;

Petiolule color: Variable, nearest RHS 178B to between RHS 177C and RHS 160A;

Inflorescence: Compound corymb; flowering in the upper 20 cm and to about 20 cm wide; with about 22 branches, branches with to about 10 flowers; inflorescence with about 75 flowers;

Flower buds one day prior to starting to open: Ellipsoidal; smooth, glabrous, about 6 mm long and 4 mm diameter;

Bud color one day prior to starting to open: Sepals heavily maculate in the longitudinal center with spots less than 0.01 mm diameter of nearest RHS 172A, sepal margins nearest RHS 20A and expose petals nearest RHS 16C;

Flower: Perfect; complete; actinomorphic;

Flower size: To about 37 mm in diameter and 13 mm in depth;

Flower fragrance: None detected;

Lastingness of flowers: About 7 days from initial opening dehiscence; self-cleaning;

Petals: Four; spurs; lanceolate; arcuate outwardly and curving toward center axis; apex narrowly acute; base truncate, adnate on axial portion; adaxial and abaxial smooth, glabrous and slightly lustrous; to about 16 mm long natural, 18 mm long straightened, and about 7 mm across at opening;

Petal color: When opening and fully open spur adaxial and abaxial nearest RHS 9B along basal edge and in the center heavily maculate with spots less than 0.01 mm diameter of nearest RHS 42A, with apical 3 to 5 mm nearest RHS 13A; before dropping spots lighten to nearest RHS 180C and basal 4 mm to between RHS 5A and RHS 5B;

Pedicel: Cylindrical; micro-glandular; to about 24 mm long and 0.3 mm diameter; average about 17 mm long and 0.3 mm diameter at base;

Pedicel color: Distally between RHS 146A and RHS NN137C, proximally nearest RHS 137A;

Peduncle: Cylindrical; stiff; strong; glabrous to sparsely puberulent; slightly lustrous; with to about 12 branches; main peduncle aspect upright to slightly arching; proximal branches outwardly to about 45 degrees from main axis and distal branches to about 90 degrees from main axis; flowering in the distal 30 cm long and to 26 cm across; branches to about 12 cm long and 1.5 mm diameter at base;

Peduncle color: Proximal portion nearest RHS 146B lightly maculate with nearest RHS N186B, distal portion and branches between RHS 146C and RHS 146B, with branch nodes nearest RHS N186A;

Sepals: Four; rotate; single whorl; lanceolate; smooth, glabrous and matte; attenuate base, acute apex; margin entire; to about 10 mm long and 6 mm across;

Sepal color: Adaxial and abaxial nearest RHS 9B along margin and apical 3 mm, and in the center moderately to heavily maculate with spots less than 0.01 mm diameter of nearest RHS 42A;

Androecium: Four;

*Anther*.—Four; oblong; longitudinal; basifixed; extrose; to about 1.5 mm long and 1 mm across; color prior to opening nearest RHS 144A.

*Filaments*.—Four; applanate proximally; about 4 mm long and 1 mm wide at base, narrowing distally; color nearest RHS 160C.

*Pollen*.—Abundant; color nearest RHS 144B.

Gynoecium: Single; superior;

*Style*.—Cylindrical; glabrous; about 3 mm long and 0.3 mm diameter; color nearest RHS 145B.

*Stigma*.—Oblate spheroid; glabrous; to about 0.2 mm long and about 0.7 mm diameter; color nearest RHS 145C.

*Ovary*.—Oblong; glabrous; smooth; to about 3 mm long and 1 mm diameter; color between RHS 144A and RHS 144B.

Fruit: Oblong cylindrical dehiscent capsule; to about 7 mm long and 1.5 mm diameter; with a truncate base and apical beak about 3 mm long and 0.5 mm diameter; color as maturing nearest RHS 144A;

Seeds: About 12 seeds per capsule; about 1 mm long and 0.5 mm across; color nearest RHS 157D;

Resistance: Not been tested or shown to be susceptible or resistance to pests and diseases common to *Epimedium;*

Hardiness: The new plant has survived USDA winter hardiness to at least zones 5 to 8 but has not been tested yet beyond these temperatures.

It is claimed:

1. A new and distinct cultivar of *Epimedium* plant named 'Carnival Clown' as herein described and illustrated.

* * * * *